United States Patent [19]

Rakowicz-Szulczynska et al.

[11] Patent Number: 5,296,348

[45] Date of Patent: Mar. 22, 1994

[54] METHODS FOR SCREENING MONOCLONAL ANTIBODIES FOR THERAPEUTIC USE

[75] Inventors: Ewa Rakowicz-Szulczynska, Philadelphia; Hilary Koprowski, Wynnewood, both of Pa.

[73] Assignee: The Wistar Institute of Anatomy and Biology, Philadelphia, Pa.

[21] Appl. No.: 352,258

[22] Filed: May 16, 1989

[51] Int. Cl.$^5$ .................. C12Q 1/68; G01N 33/566; C07H 21/02; C12N 15/00

[52] U.S. Cl. .................................. 435/6; 435/71; 436/501; 436/503; 436/508; 436/514; 436/531; 436/548; 536/23.1; 536/23.5; 935/33; 935/34; 935/43

[58] Field of Search ................ 435/6, 7.1, 91; 436/531, 548, 501, 503, 508, 514; 424/85; 536/23.1, 23.5; 935/33, 34, 43

[56] References Cited

U.S. PATENT DOCUMENTS

4,742,000  5/1988  Greene ........................... 436/501

OTHER PUBLICATIONS

Rakowicz-Szulczynska and Horst, *Archivum Immunologiae et Therapiae Experimentalis*, 32:659–663. (1984).

Rakowicz-Szulczynska and Horst, *Acta Antropenetica*, 7,(4):283–288 (1983).

H. Bender et al, *Cancer Research*, 52:121–126 (Jan. 1, 1992).

L. W. Brady et al, *Antibody, Immunoconjugates, and Radiopharmaceuticals*, 3(3):169–179 (1990).

H. P. Kalofonos et al, *J. Nucl. Med.*, 30:1636–1645 (1989).

L. W. Brady et al, *Front. Rad. Ther. Oncol.*, 24:151 (1990).

Rakowicz-Szulczynska, et al., *Genetica Polonica*, vol. 26, No. 1, 1985, pp. 1–8.

Ross, et al., *P.N.A.S.*, U.S.A., vol. 81, pp. 6681–6685, Nov. 1984.

Rakowicz-Szulczynska et al., "Uptake of Intraperitoneally Injected [$^{125}$I] IgG by Spleen, Liver, Kidney and Heart Cells of Rat", *Genetica Polonica*, vol. 26, No. 1, 1985, pp. 5–12.

Rackowicz-Szulczynska et al., *Arch. Biochem. Biophys.* Feb. 1, 1989, 268(2) pp. 456–464 (see abstract).

H. Kaprowski et al, *Proc. Natl. Acad. Sci. USA*, 81:216–222 (1983).

M. Herlyn et al, *Adv. Cancer Res.*, 49:189–221 (1987).

H. Koprowski et al, *Somat. Cell. Mol. Genet.*, 11:297–302 (1985).

H. F. Sears et al, *Contr. Oncol.*, 19:180–192 (1984).

H. Ross et al, *Proc. Natl. Acad. Sci. USA*, 81:6681–6685 (1984).

P. M. Grob et al, *J. Biol. Chem.*, 260:8044–8049 (1985).

U. Murthy et al, *Arch. Biochem. Biophys.*, 252:549–560 (1987).

*Primary Examiner*—Margaret Parr
*Assistant Examiner*—Bradley L. Sisson
*Attorney, Agent, or Firm*—Howson and Howson

[57] ABSTRACT

The present invention provides a method for selecting from among many monoclonal antibodies capable of binding to a surface antigen on a tumor cell, the antibody which also can internalize into the cell and exert an appropriate molecular effect on the level of gene regulation in the tumor cell. Such antibodies can most effectively be employed to damage the tumor cell.

2 Claims, No Drawings

METHODS FOR SCREENING MONOCLONAL ANTIBODIES FOR THERAPEUTIC USE

This invention was made with government support under Grant Numbers CA-25872, CA-44877 and CA-10815 from the National Institutes of Health. The government has certain rights in this invention.

The present invention relates to the use of monoclonal antibodies as therapeutic agents for the treatment or destruction of cancerous tumors. More particularly, this invention provides a method for selecting a monoclonal antibody capable of binding to a surface antigen on a selected tumor cell, which also can internalize into the cell and exert an appropriate molecular effect on the level of gene regulation in the tumor cell. When conjugated with a radioactive or toxin ligand, the antibody selected by this method can most effectively be employed in an appropriate dosage to damage the tumor cell.

BACKGROUND OF THE INVENTION

Monoclonal antibodies directed against tumor-associated antigens expressed on the tumor cell surface and therefore capable of targeting such tumors have found application in the immunodiagnosis and immunotherapy of human tumors. For example, a monoclonal antibody directed against such an antigen may be tagged with a radioactive, or other, detectable label and used for cancer diagnosis. Additionally, therapeutic uses of monoclonal antibodies are being developed by labelling the antibody with a quantity of a radioactive isotope or a toxic ligand to damage or destroy the targeted tumor.

The interaction of certain monoclonal antibodies directed against tumor cells with cell surface antigens is well documented. See, for example, H. Koprowski, et alli, *Proc. Natl. Acad. Sci. USA*, 81:216-222 (1983) [Koprowski I]; M. Herlyn et al, *Adv. Cancer Res.*, 49:189-221 (1987) [Herlyn I]; H. Koprowski, et alli, *Somat. Cell. Mol. Genet.*, 11:297-302 (1985) [Koprowski II]; and H. F. Sears, et alli, *Contr. Oncol.*, 19:180-192 (1984) [Sears I] among others.

A special class of anti-tumor monoclonal antibodies is represented by those antibodies that recognize surface receptors for growth factors. See, e.g., H. Ross, et alli, *Proc. Natl. Acad. Sci. USA*, 81:6681-6685 (1984) [Ross I]; P. M. Grob, et alli, *J. Biol. Chem.*, 260:8044-8049 (1985); and U. Murthy, et alli, *Arch. Biochem. Biophys.*, 252:549-560 (1987) among others.

In present immunotherapy, the selection of a monoclonal antibody for use in treating a certain tumor type is based on the binding of the monoclonal antibody to the cell surface antigen against which the antibody is directed. Monoclonal antibodies, particularly, mouse monoclonal antibodies of the IgG2A isotype, have been observed to destroy human cancer cells implanted in athymic nude mice. The tumoricidal effect seems to be mediated by the monoclonal antibody through interaction with Fc receptors of mouse or human macrophages. Monoclonal antibodies of an isotype other than IgG2A which do not interact with Fc receptors have not been observed to mediate destruction of cancer cells. The presently employed methods of selecting a monoclonal antibody for immunotherapy deal with interaction between the monoclonal antibody and surface of the cell only.

These present methods for selecting an antibody for therapeutic treatment are inadequate in view of recent scientific observations that some antibodies simply attach to the antigen, while other monoclonal antibodies are taken up intracellularly and translocated to the cell nucleus. For example, one monoclonal antibody 425 (IgG2A) directed against the EGF receptor was observed to be translocated to the nucleus in intact cells instead of the original ligand. Another monoclonal antibody directed against the Y determinant expressed on EGF receptor of tumor cell lines was translocated into the nucleus of colorectal carcinoma but not epidermoid carcinoma cells [E. M. Rakowicz-Szulczynska, et alli, *Arch. Biochem. Biophys.*, 268:456-464 (1989)].

These observations suggest that certain monoclonal antibodies may be more desirable than others for therapeutic activity in tumor cells and that the present methods for selection of antibodies for therapeutic use are inadequate.

Additional disadvantages in the present use of monoclonal antibodies in immunotherapy include the current lack of knowledge of dosage levels of antibody and radioactive or toxic ligands attached thereto. In current practice the dosage of a labelled antibody to which is attached a radioactive label or toxin to be administered to the patient is simply grossly estimated based on the size of the patient's tumor.

Preferably, antibody therapy should employ a sufficient dosage to kill the tumor cell to which the antibody attaches and yet decrease as much as possible the side effects of the radioactivity or toxin on the healthy tissue of the patient. Inaccurate dosage can often result in the patient being exposed to either excessive amounts of radioactivity or toxin with their attendant serious side effects, or inadequate amounts of radioactivity or toxin to destroy the tumor.

There exists therefore a need in the field of immunotherapy for methods for the selection of appropriate monoclonal antibodies in suitable dosages for the treatment of certain tumors.

SUMMARY OF THE INVENTION

The present invention provides novel methods for the rapid screening of a number of monoclonal antibodies (MAbs) directed against a tumor-associated antigen on a selected tumor cell, e.g., a biopsy tissue sample, to identify the MAb most effective for therapeutic treatment.

As one aspect the present invention provides a method for identifying from a number of MAbs known to bind a surface antigen on a particular tumor cell, those MAbs which are internalized, translocated to the nucleus and bound to the chromatin of that tumor cell. The method includes incubating each MAb having associated therewith a detectable label with a sample of selected tumor cells, e.g., cells from a patient's biopsy. The cells are fractionated into cytoplasm, nucleoplasm, nuclear membrane and chromatin cell fractions and the amount of label bound to each cell fraction is detected. The number of molecules of each MAb taken up by each cell fraction is measured; and a selected MAb which is translocated to the nucleus and bound to the chromatin is identified by comparing these numbers for each tested MAb. The method of the invention further includes selecting a MAb from among the tested MAbs which is translocated to the nucleus in the greatest amount.

According to another aspect of this invention, the method permits identification of a MAb which, upon internalization by the tumor cell, acts on a translational or transcriptional level to effect the cell's metabolism and thereby inhibit cell growth. The steps of this method include first incubating a sample of tumor cells with a MAb in the presence of [$^3$H] uridine or [$^3$H] thymidine. The amount of radioactivity of [$^3$H] uridine incorporated into RNA or [$^3$H] thymidine incorporated into DNA in the incubated cells is compared to control cells incubated in the presence of [$^3$H] uridine or [$^3$H] thymidine only. Cells incubated with a MAb which inhibits RNA synthesis and/or DNA synthesis in the tumor cell are identified by a decrease in cellular uptake of [$^3$H] uridine or [$^3$H] thymidine in comparison to the control cells. This method allows the identification and selection of a MAb for treatment of a tumor cell, which MAb may be used alone, without attachment of a toxic ligand to inhibit the tumor cell metabolism.

As a further aspect of this invention, the method allows identification and selection of a MAb capable of stimulating expression of a surface antigen on a selected tumor cell from a group of MAbs capable of binding to that surface antigen. The steps of this method include pre-incubating a sample of tumor cells with a selected unlabelled MAb. Tumor cells which have not been pre-incubated with each labeled MAb and the pre-incubated tumor cells are then incubated with each labeled MAb. The amount of label present in each cell fraction of the tumor cells is measured. The MAb translocated into the pre-incubated tumor cells in significantly increased number compared to its uptake in the untreated cells has shown a stimulatory effect on its antigen expression in the cell. By using the same method, a stimulatory MAb can be identified and discarded as a choice for therapeutic application for a tumor cell characterized by overexpressed surface antigen.

In a final aspect the invention provides a method for treating a patient having a tumor characterized by an underexpressed surface antigen. The patient is first treated with a low dose of unlabelled MAb identified as capable of binding to and stimulating expression of the surface antigen on the tumor cell and/or stimulating chromatin binding of this MAb by use of the aforesaid method. The patient is then treated with the same MAb having bound thereto a radioactive label or toxin. This MAb is administered in an amount sufficient to bind to the increased number of surface antigens and chromatin binding sites for this MAb in the tumor cell and destroy the tumor cell.

Other aspects and advantages of the present invention are described further in the following detailed description of preferred embodiments of the present invention

DETAILED DESCRIPTION OF THE INVENTION

The present invention provides methods for screening from among known MAbs, those antibodies which, after binding to a tumor cell surface antigen, are internalized and translocated to the nucleus of the tumor cell. Such translocated MAbs have greater potential for use in cancer therapy than MAbs which simply bind to the antigen and are not internalized. Thus the screening methods of the present invention allow selection of the optimal MAb for use in treating a particular tumor by delivering a maximal dosage of MAb, or radiolabel or toxin attached thereto. The methods of the invention also permit, perhaps even more importantly, the screening of MAbs which may act deleteriously on the tumor cell.

The methods of this invention are variously described as employing MAbs which may be labelled by attachment to a detectable label or toxic ligand. By "detectable label" is meant any conventionally employed ligand which may be attached to a MAb and is capable of detection by laboratory techniques. Directly detectable labels which may be used in the methods of this invention include, for example, iodine-125 or iodine-123. Radioactive labels can be detected by autoradiography or scintillation counting. Indirectly detectable labels may also be used in these methods, including, e.g. fluoresceine or rhodamine derivatives. The methods of the present invention are not limited by the detectable label employed in the various steps of the methods.

Additionally ligands attached to the MAbs for therapeutic treatment may also be radioactive or toxic in nature, for use in destroying the tumor cell to which the selected MAb targets and internalizes. Such toxic ligands include any conventionally employed ligand, such as a radioactive isotope or other toxic ligand which may be attached to a MAb and employed to kill or damage the tumor cell, once it is targeted by the selected MAb according to this invention. The methods of the present invention are not limited by the identify of the ligand, provided that the ligand does not inhibit internalization of the MAb.

Similarly these methods are applicable to all MAbs and tumor cells. This invention places no limitation on the MAbs which may be assayed by the methods of this invention or the tumor cells or cell surface or chromatin antigens which may be assayed by these methods. The particular MAbs and tumor cells employed in the description of this invention are illustrative only and not meant to limit the scope of these methods.

In one method of this invention, a battery of MAbs are examined for their ability not only to bind to an antigenic determinant on a selected tumor cell, but more importantly, for therapeutic use, to be translocated into the selected tumor cell and bound to a chromatin receptor. As described below in Examples 1 and 2, this method involves incubating each MAb with a sample of the target tumor cells. Presently preferred incubation conditions are approximately 37° C. at between 1 to 24 hours.

In one embodiment of this method the detection of intracellular translocation is performed employing the techniques of immunofluorescence microscopy (Example 1). In this method, each selected unlabelled MAb is incubated with the tumor cells for which treatment is desired, to permit binding of the MAb to the antigenic determinant on the tumor cell. The MAb is then washed off and the cell culture is incubated with a selected fluorescein labeled anti-MAb antibody capable of binding to the MAb, e.g., an anti-mouse MAb, if the selected MAb is a murine MAb; or an anti-human MAb, if the selected MAb is of human origin. The intracellular distribution of fluorescence of the cells treated with the selected MAb is determined using a fluorescence microscope and compared to control tumor cells treated with only the anti-MAb antibody. The degree of fluorescence detected in the cytoplasm and nucleus indicates whether the MAb was translocated.

Alternatively the target tumor cells may be incubated with the selected radioactively labeled MAb, e.g., I$^{125}$ labelled MAb, and binding permitted. Example 2 demonstrates this step. Identification of intracellular localization of the MAbs is accomplished by fractionating the cells after incubation into cytoplasm, nucleoplasm, nuclear membrane and chromatin fractions. The cell fractionation is performed as described in E. Rakowicz-Szulczynska, et alli, above, and in Co-owned, U.S. Pat. 5,100,744, which is incorporated herein by reference. The amount of label in each cell fraction is then measured, and the number of MAb molecules bound to the chromatin fraction of the tumor cell is calculated based on the signal provided by the label and using Avogadro's number. From this measurement, the radioactivity dosage transported to the nucleus by each molecule of the MAb is calculated, and thus the number of MAb molecules needed to deliver an effective radioactive or toxic dosage necessary to kill the tumor of the patient can be determined with accuracy.

When a number of MAbs are screened in this way against a particular tumor cell, a MAb may be selected which is translocated most efficiently into the cell. The MAbs capable of translocation are compared for greatest efficiency of binding to the nuclear fraction, and a MAb selected for treatment which demonstrates the greatest number of molecules translocated to the nucleus per dosage.

Finally the amount of radioactive label or toxic ligand to be attached to the selected MAb for use in treating the cell can be accurately calculated based on the number of molecules of the selected MAb which is incorporated into the cell.

Thus the dosage of MAb necessary for destruction of cancer cells by treatment with an unlabelled MAb capable of internalization, or after its conjugation with radioactive or toxic ligands, can be determined quantitatively. This method allows a much more accurate and efficient dosage to be administered to a patient undergoing MAb therapy as a treatment for cancer.

The method of this invention can also be modified to determine whether a MAb, which is capable of being translocated, has an inhibitory effect on the metabolism and growth of the target tumor cell. Thus, the method for screening MAbs for translocation according to the steps as described above, may be further modified by an additional step to indicate whether the selected MAb has tumor inhibitory action. This method includes incubating a sample of tumor cells with a MAb in the presence of [$^3$H] uridine or [$^3$H] thymidine. With [$^3$H] uridine, the incubation conditions may be 37° C. for 1 to 24 hours. For [$^3$H] thymidine the incubation conditions may be 37° C. for 3 to 5 days. According to this method, [$^3$H] uridine incorporation into RNA is measured in intact cells in the presence or absence of the MAb. Decreased incorporation of [$^3$H] uridine into RNA of cells incubated with MAb shows that this MAb has an inhibitory effect on transcription.

To establish whether a MAb translocated to the nucleus directly inhibits transcription, $^{32}$P-UTP incorporation into RNA is tested in a cell free system by incubating the isolated nuclei with $^{32}$P-UTP in the presence or absence of MAb. Decreased incorporation of $^{32}$P-UTP into RNA of cell nuclei incubated with MAb shows a direct effect of a MAb which is translocated to the nucleus on RNA synthesis.

Additionally, DNA probes for specific genes normally expressed by the tumor cell may be hybridized with RNA synthesized in intact cells or in isolated nuclei in the presence or absence of MAb. By using this method a MAb may be identified which inhibits expression of such tumor cell-expressed genes. If the MAb decreases the ribosomal DNA transcription as described for ME491 in Example 4, the MAb has inhibitory effect on cell growth and may be used therapeutically in unlabelled form.

MAbs which, when translocated to the nucleus, do not inhibit ribosomal RNA synthesis can be tested for inhibitory effect on cell proliferation by determining [$^3$H] thymidine uptake in the presence or absence of MAb. The decreased incorporation of [$^3$H] thymidine into cells incubated with MAb as compared to cells not incubated shows that the MAb inhibits cell proliferation. In an alternative method, the number of tumor cells growing in the presence or absence of the MAb may be directly counted in the light microscope.

Thus the selection from a number of MAbs known to bind to a selected tumor type of a MAb capable of inhibiting tumor cell growth, allows the selection for therapeutic treatment of a cancer patient with an unlabelled MAb. Use of such a MAb in therapy would significantly decrease or eliminate the potential side effects of the toxic ligands on the patient.

The method of this invention also permits the screening of MAbs for the ability to stimulate antigen expression on a selected tumor cell and in chromatin of these cells. Such MAbs also have therapeutic use against the selected tumor cell. According to this embodiment of the method of the invention, each MAb in unlabelled form is pre-incubated with a sample of target tumor cells. The incubation conditions may be about 37° C. for about 24 hours. Thereafter a second sample of the selected tumor cells which have not been incubated with the labelled MAb and the first sample of tumor cells which have been preincubated with the labelled MAb are both incubated under identical conditions. Incubation conditions for this step may include incubation at about 37° C. for 1 to 24 hours with the same MAb to which is attached a label, e.g., I$^{125}$. The cells are then fractionated as described above, and the radioactivity in these cell fractions is then measured by conventional techniques.

Any MAb which is observed to have been translocated into and bound to the chromatin of the pretreated tumor cells in significantly increased number compared to its uptake in the cells which were not preincubated has increased the expression of its cell surface and/or chromatin antigens. The results for each MAb is compared to the results for the other MAbs in the group of MAbs tested.

A MAb can be selected for therapeutic treatment of a tumor cell characterized by low expression of surface antigen according to this method. The MAb which displays increased label detection in pre-incubated cells in comparison to untreated cells, thereby induces maximal expression of the cell surface antigen and/or chromatin antigen. This MAb would be indicated for use, for example, if the level of tumor-associated antigen on the tumor cell surface is too low to obtain an adequate therapeutic effect with a MAb directed to that antigen. This method allows selection of an appropriate MAb, which upon injection at a low dose, activates the expression of the antigen. In consequence, the increase in expression of the antigen on the tumor cell surface allows increased internalization of that or another MAb directed to that antigen, when the MAb is labelled with a radioactive or other toxic label. This method also allows such a MAb to be selected for translocation into the tumor cell in the highest amount. This method provides information which indicates the lowest effective dose of a particular MAb which may be used in treatment.

Alternatively, this method permits the identification and selection of those Mabs which do not stimulate expression of the cell surface antigen of a tumor cell which naturally demonstrates high expression of the cell surface antigen. By allowing identification of stimulatory MAbs, the method allows the selection of an appropriate MAb which either inhibits or does not activate expression of the overexpressed tumor antigen.

Using tumor tissue obtained from biopsy, the present invention allows the identification of what MAb is most appropriate for delivery of radioactivity or toxin, for use against DNA transcription and replication in the tumor or to enhance or inhibit the expression of tumor antigen in that particular patient. The methods allow an accurate estimation of the MAb dose needed to deliver to the selected tumor cell an effective minimum dose of radioactivity or toxin attached thereto capable of destroying the patient's tumor cell. Thus MAbs, screened by these methods may be selected as appropriate diagnostic or therapeutic agents.

In the case of a MAb identified as capable of stimulating antigen expression on the cell, the therapy can comprise treating the patient with a low dose of unlabelled MAb having stimulatory activity on surface antigen expression. The patient is thereafter treated with a labelled MAb capable of binding to the antigen and translocating to the nucleus in the highest amounts in comparison to untreated cells. This therapy thus allows more MAb to bind to the cell, internalize and bind with cell chromatin to destroy the genetic apparatus.

The following examples are illustrative only and do not limit the scope of the present invention. The techniques employed in the methods of the invention are demonstrated using murine MAbs. In these examples, the melanoma cell lines WM9, WM983 and WM35 [M. Herlyn, et alli, *J. Natl. Cancer Inst.*, 74:283–289 (1985) (II)], and the colorectal carcinoma cell lines SW948 and SW1116 [D. Herlyn, et alli, *Cancer Res.*, 40:717–721 (1980) (III) and M. Herlyn, et alli, *J. Immunol.*, 134:4226–4230 (1985) (111)] were grown in minimal Eagle's medium/L15(3:1) supplemented with 10% fetal calf serum.

Example 1 - Intracellular Localization of MAb ME491 by Immunofluorescence Microscopy To demonstrate detection of internalization of a MAb by a tumor cell according to one embodiment of the methods of the invention, W9 melanoma cells grown as monolayers were replated into Nunc Slide-flasks to a concentration of $5 \times 10^5$/ml and incubated 24 hours to adhere to the plastic. Murine MAb ME491 was added to a concentration of 100 ng/ml and incubation was continued for 24 hours. The medium was removed and slides were washed 3 times with phosphate-buffered saline (PBS) and fixed with 50% ethanol for 10 minutes, followed by washing with 100% ethanol for 10 minutes. Slides were washed 3 times with PBS, incubated for 1 hour at 37° C. with fluorescein-labelled goat anti-mouse immunoglobulin (IgG), washed with PBS, dried, and viewed in the microscope.

In control experiments cells which were not incubated with MAb ME491 were exposed to goat anti-mouse IgG. To eliminate cross-reactivity of goat IgG with mouse MAb, cells were incubated with MAb ME491 followed by goat anti-rabbit IgG.

After 24 hour incubation of the melanoma cells with MAb ME491, the MAb was internalized by the cells as indicated by indirect immunofluorescence techniques. The fluorescence of MAb ME491 was localized mainly in the cytoplasm. A much weaker fluorescence of the nucleus was also observed. No fluorescence was observed using goat anti-rabbit IgG instead of anti-mouse IgG which eliminates nonspecific reactivity of goat serum with MAb ME491 Cells which were not exposed to MAb ME491 did not show reactivity with anti-mouse IgG. The immunofluorescence staining was shown to be specific to internalized MAb.

Example 2 - Intracellular Localization of $^{125}$I-MAb ME491 in Intact Cells by Cell Fractionation Another embodiment of the method of the present invention using cell fractionation is described as follows. The melanoma and colorectal carcinoma cells, identified below, were incubated for 24 hours in culture medium containing $^{125}$I-murine MAb ME491 (100 ng/ml) labelled by the Iodogen method [P. J. Fraker, et alli, *Biochem. Biophys. Res. Commun.*, 80:849–853 (1978)] to a specific activity of 20 cpm/pg. Cells were then washed with PBS and fractionated into cytoplasm, nucleoplasm, nuclear membranes and chromatin as described [E. M. Szulczynska et al, cited above]. Briefly, cells were washed 3–5 times with PBS, disrupted in 0.35 M sucrose/10 mM KCl/1.5 mM MgCl$_2$/10 mM Tris-HCl, pH 7.6/0.12% TRITON®X100 [Polyethylene glycol tert-octylphenyl ether 12 mM 2-mercaptoethanol (10 ml/20×10$^6$ cells) and centrifuged at 600 X g for 10 minutes. The nuclear pellet was washed with 0.2 M sucrose/3 mM CaCl$_2$/50 mM Tris-HCl, pH 7.6. Nuclei were then extracted with 0.14 M NaCl/10 mM Tris-HCl, pH 8.3 and centrifuged at 700 × g for 10 min. The supernatant containing some of the nucleoplasm was saved to be added to another nucleoplasm-containing fraction. To isolate the chromatin, the pellet was swelled in a small amount of 1 mM Tris-HCl (pH 7.9) and centrifuged through 5 ml of 1.7 M sucrose containing 10 mM Tris-HCl, pH 7.9 (160,000 × g, 80 min). Chromatin was pelleted at the bottom of the tube, the other nucleoplasm fraction was recovered from the top, and nuclear membranes were taken at the interface. The chromatin obtained in this procedure was used for restriction nuclease digestion and immunoprecipitation with MAb ME491 as described below.

Radioactivity of $^{125}$I-MAb ME491 bound to particular fractions was measured in a Beckman gamma counter. The number of MAb molecules bound was calculated using Avogadro's number and the specific activity of MAb ME491: 160,000 (gram-molecular weight of MAb tetramer) $=6 \times 10^{23}$ molecules (Avogadro's number), 1 pg $=4 \times 10^6$ molecules $=20$ cpm (specific activity of MAb ME491), number of molecules $=$(number of pg) $\times$ ($4 \times 10^6$ molecules). Total intracellular uptake is the sum of MAb molecules in all cell fractions tested.

This fractionation of several melanoma and two colorectal carcinoma cells incubated with $^{125}$I-MAb ME491 for 24 hours confirmed the microscopic observation. 80–90% of $^{125}$I-MAb ME491 was localized in the cytoplasmic fraction of each cell. In addition, in all three melanoma cells tested (WM9, WM35, and WM983), up to 10% of internalized MAb ME491 was bound to chromatin; in SW948 colorectal carcinoma cells, up to 20% was chromatin-bound. SW1116 colorectal carcinoma cells, which do not express significant amounts of ME491 antigen, incorporated no more than 5% of the total MAb ME491 taken up by SW948 cells.

Since all human cells appear to express at least low levels of ME491 antigen [B. Atkinson et al and A. H. Ross, et alli, (II) cited above], negative control cells were not available. However, there was a strong correlation between the number of $^{125}$I-MAb ME491 molecules taken up by the cells and the amount of ME491 antigen expressed. This observation indicates the ME491 antigen-dependent internalization of MAb ME491. When the incubation with $^{125}$I-MAb ME491 was performed in the presence of a 100-fold excess of unlabelled MAb ME491, radioactivity of cell-bound MAb ME491 decreased by 75–80%.

As a control for the possibility of nonspecific adsorption of $^{125}$I-labelled MAbs to intracellular structures during cell fractionation, experiments were performed with another MAb 20.4, which specifically defects the surface NGF receptor [A. H. Ross et alli, (I) cited above] and immunoprecipitates the NGF chromatin receptor [E. M. Rakowicz-Szulczynska, et alli, cited above]. In SW948 cells, which do not express NGF receptor, MAb 20.4 was undetectable both in cytoplasm and in chromatin.

Example 3: Specificity of MAb ME491 Binding to the Chromatin

A. Chromatin Digestion with Restriction Nucleases

Electrophoretic analyses under reducing conditions of chromatin-bound $^{125}$I-MAb ME491 revealed both heavy and light chains of the same molecular weight as native MAb ME491. Thus, the MAb is taken up by the nucleus and bound to chromatin in nondegraded form. As a control for the possibility of nonspecific adsorption of $^{125}$I-MAb ME491 to the chromatin during preparation, chromatin isolated from cells incubated with $^{125}$I-MAb ME491 (100 ng/ml) for 24 h was resuspended in buffer optimal for BamHI activity and digested with BamHI (Biolabs, New England) (10 U/μg DNA) overnight at 37° C. as described [E. M. Rakowicz-Szulczynska (I) cited above]. Insoluble chromatin was pelleted, resuspended in buffer optimal for HincII (BioLabs, 10 U/μg DNA) activity and digested 2 to 24 hours at 37° C. Insoluble chromatin was pelleted and discarded. Supernatants obtained after BamHI digestion and sequential HincII digestion were analyzed electrophoretically.

$^{125}$I-MAb 491-bound restriction fragments were mixed with 50% glycerol, 0.1% bromophenol blue and electrophoretically analyzed in 4% (slab) polyacrylamide gel containing 50 mM Tris, 384 mM glycine, 2 mM EDTA, pH 8.3. The electrophoresis buffer contained 25 mM Tris, 192 mM glycine, 2 mM EDTA, pH 8.3. Gels were dried and autoradiographed. After BamHI digestion, only 10–15% of chromatin-bound $^{125}$I-ME491 was released, detectable electrophoretically as a band with a mobility similar to that of free $^{125}$I-ME491. Further digestion of the chromatin fraction remaining after BamHI digestion with HincII, released up to 75% of chromatin-bound $^{125}$I-ME491. Two $^{125}$I-ME491-bound HincII-DNA fragments of low and high mobility were identified instead of the smear expected with nonspecific binding. The lower mobility $^{125}$I-ME491 bound HincII-DNA fragment migrated in a gel at the region of 1.2 kbp and the higher mobility fragment migrated in the region of 0.6 kbp. However, because of the high molecular weight of $^{125}$I-MAb ME491 migration of both HincII DNA fragments is greatly changed and the size of those fragments was not established. Fragments of the same electrophoretic mobility were detected when the chromatin was digested with HincII alone.

B. Immunoprecipitation of a Chromatin Antigen with MAb ME491

To determine whether $^{125}$I-ME491 binds directly to DNA or to a specific chromatin protein, HincII-digested chromatin of SW948 colorectal carcinoma cells was immunoprecipitated with MAb ME491. Immunoprecipitation was carried out as described [E. M. Rakowicz-Szulczynska, et alli, (I) and (II) cited above]. Briefly, HincII-digested chromatin of SW948 cells labelled with [$^{35}$S]methionine and [$^{35}$S]cysteine (30 μCi/ml, specific activity 1000 Ci/mmol) for 18 hours was incubated with 10 mM EDTA, 0.25% bovine serum albumin (BSA) and MAb ME491 (5 μg/0.2 A$_{260}$ chromatin), P3×63Ag8 control antibody or MAb ME20.4 anti-NGF receptor [A. Ross et alli, cited above], followed by incubation with formalin-fixed Staphylococcus aureus for 1 hour at 4° C. Proteins were dissociated from S. aureus with 1% sodium dodecyl sulfate (SDS), 2 mM EDTA, 1% 2-mercaptoethanol, 30% glycerol, 0.05% bromophenol blue, 50 mM Tris-HCl (pH 8.0) and analyzed by electrophoresis in a 7.5% polyacrylamide gel with SDS according to U. K. Laemmli, *Nature (London)*, 227:680–685 (1971).

A 55 kDa band labelled with [$^{35}$S]methionine was revealed. To determine whether the 55 kDa protein was specifically precipitated by MAb ME491 or instead represented a chromatin protein which bound nonspecifically to immunoglobulins, precipitation was performed with MAb ME20.4 directed against the NGF receptor and with control antibody P3×63Ag8. No proteins were precipitated using control antibodies P3×63Ag8, or anti-NGF receptor ME20.4. Thus, it appears that $^{125}$I-MAb ME491 binds to a chromatin protein localized in specific HincII fragments.

Example 4 - Effect of MAb ME491 taken on by Nucleus on Transcription and Cell Proliferation To determine whether nuclear translocation of MAb ME491 has any effect on transcription, RNA synthesis in intact SW948 cells was measured after a 24 hour exposure to MAb ME491 and after 1 hour of exposure of nuclei isolated from the same cells.

Transcription in intact cells was studied by incubation of SW948 colorectal marcinoma cells in minimal Eagle's medium/L15 medium (3:1) supplemented with 1% fetal bovine serum, containing 0 or 100 ng/ml of MAb MA491 and 10 μCi/ml of [5,6-$^3$H]uridine (Amersham, specific activity 48 Ci/mmol) as described [E. M. RakowiczSzulczynska, cited above]. After a 24 hour incubation, cells were fractionated into cytoplasm, nucleoplasm, and chromatin as described above. Radioactivity of chromatin-bound RNA, nucleoplasmic RNA and cytoplasmic RNA was tested in the fraction precipitated with 10% trichloroacetic acid and filtered on GF/C Whatmann filters.

Transcription in isolated nuclei was studied in nuclei (5×10$^6$ nuclei in 1 ml volume) incubated for 1 hour at room temperature in 0.25 M sucrose, 20 mM Tris-HCl, pH 7.8, 10 mM MgCl$_2$, 500 ng/ml BSA, 0.3 mM each ATP, GTP, CTP and 20 μCi/ml [$^{32}$P]UTP (Amersham, specific activity 3000 mCi/mmol). Nuclei were centrifuged (600× g for 10 minutes), washed 3 times with 50 mM Tris-HCl, pH 7.5, 2.5 mM NaCl, 12.5 mM MgCl$_2$, homogenized in 1 mM Tris-HCl, pH 7.6, centrifuged through 1.7 M sucrose and fractionated into chromatin, nuclear membranes and chromatin as described above. The amount of synthesized RNA in chromatin was determined by trichloroacetic acid precipitation. RNA was isolated from nuclei incubated with [$^{32}$P]UTP in the absence or presence of NGF (5 ng/ml) by proteinase K digestion, phenol-chloroform extraction and ethanol precipitation and tested by dot-blot hybridization with plasmid pBR322 containing EcoRI fragments of human rDNA [A. Giallongo, et alli, cited above], [Dr. R. D. Schmickel, University of Pennsylvania School of Medicine].

In intact cells exposed to 100 ng/ml MAb ME491, total RNA synthesis, measured as [$^3$H]uridine incorporation into cytoplasmic, nucleoplasmic and chromatin RNA, decreased by 72%.

To determine whether MAb ME491 taken up by the nucleus directly affects transcription, RNA synthesis was tested in isolated nuclei. After a 1 hour exposure to MAb ME491, RNA synthesis in isolated nuclei, measured as incorporation of [$^{32}$P]UTP decreased by 62%. Thus, MAb ME491 taken up by the nucleus and bound to chromatin directly inhibited transcription. Since ribosomal RNA represents the bulk of synthesized RNA, the effect of MAb ME491 taken up by the nucleus on rRNA synthesis was analyzed. [$^{32}$P]UTP RNA synthesized in SW948 cell nuclei in the presence or absence of MAb ME491 was hybridized to plasmid DNA containing the ribosomal DNA. Transcription levels of RNA in nuclei incubated with MAb ME491 decreased by 67% as compared with levels in nuclei of control cells. Thus, MAb ME491 taken up by nucleus and bound to chromatin directly inhibited transcription of ribosomal RNA genes. In control experiments MAb ME20.4 directed against the NGF receptor (not expressed by SW498 cells) did not change total RNA synthesis.

To determine the effect of MAb 491 on cell proliferation, cells were incubated 3–4 days in the presence of [6-$^3$H]thymidine (10 μCi/ml, specific activity 24Ci/mmol, Amersham) and presence or absence of MAb ME 491 (100 ng/ml). After 3 days of incubation with MAb ME 491 cell proliferation measured as [$^3$H] thymidine incorporation into DNA decreased by 60%.

Example 5: MAb Selection by the Present Method.

This example demonstrates the use of the methods of the present invention in selecting from among a group of murine MAbs produced by the Wistar Institute of Anatomy and Biology, those which are internalized, translocated to the nucleus and bound to the chromatin.

Tumor cell lines for use in this example include A 431, a human epidermoid carcinoma cell line; SKBR-5, a human breast carcinoma cell line; SW 948, SW 1116, and SW 707, all human colorectal carcinoma cell lines; and A 875, HS 294, WM 266-4, WM 9, WM 983, WM 164 and WM 35, all human melanoma cell lines. The cells were incubated with $^{125}$I-MAb (100 ng/ml) for each of the MAbs labeled below for 2 hours (a), 24 hours (b) or 4 hours (c). The cells were then fractionated into cytoplasm and chromatin as described in the Example 2.

The results reported in the Table below demonstrate that most of the tested MAbs directed against the cell surface proteins of certain tumor cells are internalized and translocated to the nucleus. The amount of internalized and chromatin-bound MAb is different in different cell lines of the same tumor. Additionally it was observed that MAb 20.4 directed against the NGF cell surface receptor is internalized without a nuclear translocation.

MAbs directed against the cell surface carbohydrate determinants are in general not internalized, with one exception. MAb Br 15-6A is internalized and translocated to the nucleus in several colorectal carcinoma cell lines and breast carcinoma cell line SKBR-5.

TABLE 1

Intracellular distribution of $^{125}$I-MAbs after incubation with different cell lines

| MAb | Antigen Recognized | Cell Line | Molecules/cell Cytoplasm | Molecules/cell Chromatin |
|---|---|---|---|---|
| 425 a (IgG2a) | EGF receptor | A 431 | 180,000 | 2,100 |
| | | SW 948 | 73,600 | 1,750 |
| | | WI 38 | 27,000 | 300 |
| ME 20.4 b (IgG1) | NGF receptor | A 875 | 2,000 | undetectable |
| | | HS 294 | 2,500 | undetectable |
| | | SW 707 | 450 | undetectable |
| GA 73.3 c (IgG2a) | cell surface protein on colon carcinoma | SW 707 | 222,865 | 7,050 |
| | | SW 1116 | 79,500 | 4,500 |
| | | SW 948 | 320 | 45 |
| | | WM 266-4 | undetectable | |
| ME 491 b (IgM) | cell surface glycoprotein | SW 948 | 32,000 | 9,250 |
| | | SW 1116 | 2,685 | 450 |
| | | WM 983 | 52,700 | 5,550 |
| | | WM 9 | 35,450 | 3,800 |
| | | WM 35 | 13,000 | 1,750 |
| ME 49.9 a (IgG1) | cell surface protein | WM 266-4 | undetectable | |
| | | WM 164 | undetectable | |
| | | A 875 | 1,300 | 200 |
| | | SW 1116 | 9,500 | 500 |
| CO 3019 a,b,c (IgG1) | carbohydrate | WM 266-4 | undetectable | |
| | | WM 164 | undetectable | |
| | | SW 1116 | undetectable | |
| BR 15-6A a (IgG2A) | carbohydrate, Y determinant | A 431 | undetectable | |
| | | SW 948 | 29,500 | 17,100 |
| | | SW 1116 | 17,750 | 3,000 |
| | | SW 707 | 7,000 | 1,000 |
| | | SKBR-5 | 175,840 | 27,530 |
| BR 55.2 c (IgG2A) | carbohydrate Y determinant | SW 948 | undetectable | |
| | | SW 707 | undetectable | |
| ME 361 c (IgG2A) | carbohydrate GD$_2$/GD$_3$ | WM 266-4 | undetectable | |
| | | WM 9 | undetectable | |
| | | A 875 | undetectable | |
| | | SW 1116 | undetectable | |
| | | SW 948 | undetectable | |

Example 6: Induction of Cell Surface and Chromatin Antigen Expression by a MAb

To determine the effect of a MAb on the expression of the cell surface and the chromatin antigen recognized by it, SW948 colorectal carcinoma cells and WM 266-4 melanoma cells were preincubated for 24 hours with 50 ng/ml of the each MAb indicated in the Table below, followed by incubation with $^{125}$I-MAb (100 ng/ml) for 4 hours (a); 1 hour (b) or 24 hours (c). The method of incubation and cell fractionation was described in Example 2.

SW 948 colorectal carcinoma cell line represents an example of a cell line characterized by low expression of the antigen recognized by MAb GA 73.3. Other colorectal carcinoma cell lines SW 1116 and SW 707 (see Table 1, Example 5) exhibit high expression of this antigen. After 24 hours preincubation with GA 73.3, the total uptake of $^{125}$I-MAb GA 73.3 by SW 948 cells increased 8 fold. Chromatin binding of $^{125}$I-MAb GA 73.3 in cells preincubated with MAb GA 73.3 was 25 fold higher than in cells not preincubated. Therefore, MAb GA 73.3 represents a MAb which may be used for activation of the corresponding antigen expression.

In contrast, expression of ME 491 antigen on SW 948 colorectal carcinoma cells is high (see also Table 1). Preincubation of cells with MAb ME 491 slightly stimulated uptake of $^{125}$I-MAb ME 491 into the cytoplasm, however, chromatin binding in cells preincubated was 4 fold lower. The results show that ME 491 saturated the chromatin antigen, expression of which is not stimulated by MAb ME 491.

ME 361 directed against the carbohydrate antigen is not internalized and does not activate $^{125}$I-MAb ME 361 internalization in SW 948 cells.

WM 266-4 is a cell line which does not express a detectable level of antigen for MAb 49.9. After preincubation for 24 hours with this MAb, it incorporates very high amounts of this MAb into the cytoplasm and into the chromatin. Even totally undetectable antigen expression may be induced by preincubation with unlabelled MAb.

TABLE 2

Uptake of $^{125}$I-MAbs before (A) and after (B) preincubation of SW 948 colorectal carcinoma cells and WM 266-4 melanoma cells with unlabelled MAbs

| | intracellular uptake molecules/cell | | | | | |
|---|---|---|---|---|---|---|
| | A | | B | | B/A | |
| MAb | cyto-plasm | chro-ma-tin | cyto-plasm | chroma-tin | cyto-plasm | chro-ma-tin |
| SW 948 | | | | | | |
| GA 73.3$^a$ | 300 | 40 | 1,600 | 1,000 | 5.3 | 25 |
| ME 491$^b$ | 3,800 | 1,000 | 5,320 | 220 | 1.4 | 0.2 |
| ME 361$^c$ | undetectable | | undetectable | | | |
| WM 266-4 | | | | | | |
| ME 49.9$^a$ | undetectable | | 16,180 | 5,250 | >16,180 | >5,250 |

Cells were incubated with $^{125}$I-MAb for 4 hours (a), 1 hour (b) or 24 hours (c).

Numerous modifications and variations of the present invention are included in the above-identified specification and are expected to be obvious to one of skill in the art. For example, the methods of the present invention may be used on other MAbs not specifically identified in this specification. As described by the specification, these methods are particularly adapted for use in screening any number of MAbs for any number of tumor cells, whether presently known or to be designed, identified or developed in the future. The diagnostic potential of this method is clearly applicable to all such antibodies and tumor cells. Such modifications and alterations to the compositions and processes of the present invention are believed to be encompassed in the scope of the claims appended hereto.

What is claimed is:

1. A method for selecting a monoclonal antibody specific for a surface antigen on a tumor cell, said antibody characterized by the ability to internalize into the nucleus of said cell where said antibody is selected from a group of monoclonal antibodies capable of binding to said surface antigen, said method comprising the steps of:
    (a) providing a first sample and a second sample of said tumor cells and dividing said group of antibodies into a first sample and a second sample of monoclonal antibodies and pre-incubating the first sample of said tumor cells with a first sample of said monoclonal antibodies;
    (b) labelling the second sample of said monoclonal antibodies with a radioactive label;
    (c) incubating the pre-incubated first sample of tumor cells and the second non pre-incubated, sample of said tumor cells of step (a) with each said labeled monoclonal antibody;
    (d) fractionating the cells and measuring the amount of the label present in each cell fraction of the first and second sample of said tumor cells;
    (e) identifying the monoclonal antibody taken into the pre-incubated tumor cells in increased number compared to its uptake in the second sample of cells and in comparison to the uptake of the other labeled monoclonal antibodies in said group; and
    (f) selecting the monoclonal antibody which is characterized by an increased amount of label in said pre-incubated tumor cells in comparison to said second sample of tumor cells, said increased amount of label being the result of that antibody's ability to induce expression of the cell surface antigen or chromatin antigen and to be translocated into the cell in comparatively highest quantities.

2. A method for identifying a monoclonal antibody characterized by having an anti-transcriptional and/or anti-replicational intracellular effect on cell metabolism, said method comprising:
    (a) incubating a sample of tumor cells with at least one selected monoclonal antibody in the presence of radioactivity labeled uridine or radioactively labeled thymidine;
    (b) measuring the amount of the radioactively labeled uridine incorporated into RNA or radioactively labeled thymidine incorporated into DNA in said cell compared to control cells incubated in the presence of radioactively labeled uridine or radioactively labeled thymidine only;
    (d) identifying a monoclonal antibody which inhibits RNA synthesis and/or DNA synthesis in said cell, by identifying a decrease in cellular uptake of radioactively labeled uridine or radioactively labeled thymidine by cells incubated with said monoclonal antibody in comparison to control cells, wherein inhibition of RNA synthesis is indicative of an anti-transcriptional effect and inhibition of DNA synthesis is indicative of an anti-replicational effect.

* * * * *